US011534493B2

(12) United States Patent
Osborne

(10) Patent No.: US 11,534,493 B2
(45) Date of Patent: *Dec. 27, 2022

(54) PHARMACEUTICAL COMPOSITIONS OF ROFLUMILAST IN AQUEOUS BLENDS OF WATER-MISCIBLE, PHARMACEUTICALLY ACCEPTABLE SOLVENTS

(71) Applicant: ARCUTIS, INC., Menlo Park, CA (US)

(72) Inventor: David W. Osborne, Fort Collins, CO (US)

(73) Assignee: Arcutis Biotherapeutics, Inc., Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/712,900

(22) Filed: Sep. 22, 2017

(65) Prior Publication Data
US 2019/0091333 A1 Mar. 28, 2019

(51) Int. Cl.
A61K 47/10 (2017.01)
A61K 9/00 (2006.01)
A61K 9/06 (2006.01)
A61K 31/44 (2006.01)

(52) U.S. Cl.
CPC ............ A61K 47/10 (2013.01); A61K 9/0014 (2013.01); A61K 9/0019 (2013.01); A61K 9/06 (2013.01); A61K 31/44 (2013.01); A61K 2300/00 (2013.01)

(58) Field of Classification Search
None
See application file for complete search history.

(56) References Cited

U.S. PATENT DOCUMENTS

| 5,374,661 A * | 12/1994 | Betlach, II | A61K 9/0014 514/772.4 |
|---|---|---|---|
| 5,712,298 A | 1/1998 | Amschler | |
| 7,951,398 B2 | 5/2011 | Dietrich et al. | |
| 8,536,206 B2 | 9/2013 | Kohl et al. | |
| 9,205,044 B2 | 12/2015 | Linder | |
| 9,649,302 B2 | 5/2017 | Vakkalanka | |
| 2006/0084684 A1* | 4/2006 | Bolle | A61P 17/14 514/352 |
| 2006/0153905 A1* | 7/2006 | Carrara | A61K 9/0014 424/449 |
| 2006/0204526 A1* | 9/2006 | Lathrop | A61K 9/0014 424/400 |
| 2007/0259009 A1 | 11/2007 | Linder | |
| 2007/0287689 A1* | 12/2007 | Harada | A61K 31/277 514/171 |
| 2008/0039405 A1* | 2/2008 | Langley | A61K 9/0014 514/29 |
| 2008/0280958 A1 | 11/2008 | Bolle et al. | |
| 2009/0104132 A1* | 4/2009 | Segura-Orsoni | A61K 9/0014 424/59 |
| 2011/0117182 A1* | 5/2011 | Ahluwalia | A61K 8/466 424/450 |
| 2012/0252793 A1 | 10/2012 | Bream et al. | |
| 2013/0005816 A1* | 1/2013 | Chen | A61K 9/0014 514/570 |
| 2013/0217742 A1* | 8/2013 | Yang | A61K 9/0014 514/398 |
| 2014/0275265 A1* | 9/2014 | Mattison | A61K 9/0014 514/570 |
| 2014/0296191 A1 | 10/2014 | Patel et al. | |
| 2014/0303215 A1 | 10/2014 | Bolle et al. | |
| 2015/0099752 A9 | 4/2015 | Bernal Anchuela et al. | |
| 2015/0297601 A1 | 10/2015 | Henkin | |
| 2017/0152273 A1 | 6/2017 | Merchant et al. | |
| 2017/0266289 A1* | 9/2017 | Lipari | A61K 47/10 |

FOREIGN PATENT DOCUMENTS

| CN | 1655782 A | 8/2005 | |
|---|---|---|---|
| EP | 1511516 A1 | 3/2005 | |
| WO | 9501338 A1 | 1/1995 | |
| WO | WO-9810768 A1 * | 3/1998 | ........... A61K 9/0014 |
| WO | 2013030789 A1 | 3/2013 | |
| WO | 2014055801 A1 | 4/2014 | |
| WO | 2015132708 A1 | 9/2015 | |

(Continued)

OTHER PUBLICATIONS

Shakeel et al. "Solubilization behavior of paracetamol in Transcutol—water mixtures at (298.15 to 333.15) K," Journal of Chemical & Engineering Data 58:3551-3556, 2013.*
Wikipedia "Corticosteroid," last edited Nov. 15, 2019; https://en.wikipedia.org/wiki/Corticosteroid.*
SpecialChem "Ethoxydiglycol," printed 2019; https://cosmetics.specialchem.com/inci/ethoxydiglycol.*
Osborne "Diethylene glycol monoethyl ether: an emerging solvent in topical dermatology products" Journal of Cosmetic Dermatology 10:324-329, 2011.*

(Continued)

Primary Examiner — Ileana Popa
Assistant Examiner — Alissa Prosser
(74) Attorney, Agent, or Firm — Rothwell, Figg, Ernst & Manbeck, P.C.

(57) ABSTRACT

The low aqueous solubility of roflumilast in parenteral preparations and topical emulsions, suspensions, gels or solutions can be improved by including a blend of water-miscible solvents in the pharmaceutical composition. The blend of water-miscible solvents can include diethylene glycol monoethyl ether (Tradename Transcutol®; abbreviated DEGEE) and water. The ratio of diethylene glycol monoethyl ether to water is from 1:10 to 20:1. The resulting composition has improved bioavailability and efficacy and can be used to inhibit phosphodiesterase 4 in a patient in need of such treatment.

2 Claims, 5 Drawing Sheets
(5 of 5 Drawing Sheet(s) Filed in Color)

(56) References Cited

FOREIGN PATENT DOCUMENTS

| WO | WO-2016033308 A1 * | 3/2016 | ............. A61K 47/32 |
| WO | WO-2017216738 A1 * | 12/2017 | ............. A61K 47/08 |

OTHER PUBLICATIONS ip.com translation KR 1999-0015251 A, printed 2022 (Year: 2022).*
Snape et al., "A phase I randomized trial to assess the effect on skin infiltrate thickness and tolerability of topical phosphodiesterase inhibitors in the treatment of psoriasis vulgaris using a modified psoriasis plaque test", British Journal of Dermatology (2016) 175, pp. 479-486.
Pudipeddi et al., "Trends in Solubility of Polymorphs", Journal of Pharmaceutical Sciences, May 2005, vol. 94, Issue 5, pp. 929-939, Abstract only.
Patzelt et al., "Hair follicles, their disorders and their opportunities", Drug Discovery Today: Disease Mechanisms, vol. 5, Issue 2, Summer 2008, pp. e173-e-181.
Akhtar et al., "Exploring preclinical and clinical effectivenss of nanoformulations in the treatment of atopic dermatitis: Safety aspects and patent reviews", Bulletin of Faculty of Pharmacy, Cairo University 55 (2017), 1-10.
Karande et al., "Enhancement of transdermal drug delivery via synergistic action of chemicals", Biochimica et Biophysica Acta, 1788 (2009), pp. 2632-2373.
Lorimer, "Thermodynamics of solubility in mixed solvent systems", Pure & Appl. Chem., 1993, vol. 65, 2, pp. 183-191.
Minghetti et al., "Ex Vivo Study of Transdermal Permeation of Four Diclofenac Salts from Different Vehicles", Journal of Pharmaceutical Sciences, vo. 96, No. 4, Apr. 2007, pp. 814-823.
Nair et al., "Basic considerations in the dermatokinetics of topical formulations", Brazilian Journal of Pharmaceutical Sciences, vol. 43, No. 3, Jul./Sep. 2013, pp. 423-434.
Osborne, "Diethylene glycol monoethyl ether: an emerging solvent in topical dermatology products", J. Cosmet Dermatol, Dec. 2011, 10(4), pp. 324-329, Abstract.
Pathan et al., "Chemical Penetration Enhancers for Transdermal Drug Delivery Systsms", Tropical Journal of Pharmaceutical Research, Apr. 2009, 8(2), pp. 173-179.
Sikarra et al., "Techniques for Solubility Enhancement of Poorly Soluble Drugs: An Overview", Journal of Medical Pharmaceutical and Allied Sciences, (2012), 01; pp. 1-22.
Tradename (roflumilast) Tablets NDA 22-522, Summary of Basis for the Recommended Action from Chemistry, Manufacturing, and Controls, Forest Research Institute, Inc., Reference ID 2901509, 3 pages, original submission 2009.
International Search Report and Written Opinion cited in PCT/US2018/051691 dated Nov. 22, 2018, 11 pages.
Translation of Office Action for Chinese Patent Application No. 201810581282.7 dated Oct. 22, 2019, 13 pages with Abstract.
International Preliminary Report on Patentability and Written Opinion cited in PCT/US2018/051691 dated Apr. 2, 2020, 8 pages.
Examination Report cited in India Application No. 202047016247 dated Jun. 28, 2021, 4 pages.

* cited by examiner

PHARMACEUTICAL COMPOSITIONS OF ROFLUMILAST IN AQUEOUS BLENDS OF WATER-MISCIBLE, PHARMACEUTICALLY ACCEPTABLE SOLVENTS

FIELD OF THE INVENTION

The invention pertains to pharmaceutical compositions of roflumilast in blends of water-miscible, pharmaceutically acceptable solvents. More particularly, the invention involves the discovery that roflumilast, a drug with poor water solubility, exhibits unexpectedly high solubility in such solvent blends.

BACKGROUND OF THE INVENTION

Roflumilast is known to be suitable as a bronchial therapeutic agent as well as for the treatment of inflammatory disorders. Compositions containing roflumilast are used in human and veterinary medicine and have been proposed for the treatment and prophylaxis of diseases including but not limited to: inflammatory and allergen-induced airway disorders (e.g. bronchitis, asthma, COPD); dermatoses (e.g. proliferative, inflammatory and allergen induced skin disorders), and generalized inflammations in the gastrointestinal region (Crohn's disease and ulcerative colitis).

Roflumilast and its synthesis were described in U.S. Pat. No. 5,712,298 (the "'298 patent"), incorporated herein by reference.* It has long been recognized that pharmaceutical compounds having phosphodiesterase (PDE)-inhibiting properties, such as roflumilast, are useful for treating psoriasis and atopic dermatitis ('298 patent, col 11 lines 52-61) and other chronic inflammatory and allergen-induced dermatoses. For treatment of such dermatoses, roflumilast emulsions, suspensions, gels or solutions for topical application have been described ('298 patent, col 12, lines 37-64). Although oral tablets of roflumilast have been commercialized, the low aqueous solubility of the compound has been reported to be only 0.53 mg/l at 21° C. in WO95/01338 (corresponding to the '298 patent and incorporated herein by reference). This low aqueous solubility has been problematic for the development of parenteral preparations and topical emulsions, suspensions, gels or solutions containing water. In U.S. Pat. No. 9,205,044 (incorporated herein by reference), the poor water solubility of roflumilast was overcome by using an alkoxylated fat, specifically polyoxyethylated 12-hydroxystearic acid, as a co-solvent for parenteral administration. In EP 1511516B1 (corresponding to published U.S. application Ser. No. 14/075,035 incorporated herein by reference), the low water solubility of roflumilast was overcome in topical emulsion (cream) formulations by formulating with polyethylene glycol 400 (PEG 400) in concentrations over 62% (w/w) while keeping water weight percentages under 10%.

*Unless otherwise indicated, references incorporated herein by reference are incorporated in their entireties for all purposes.

Topical application of potent pharmacological agents like roflumilast for treating skin diseases has been found to provide superior delivery, lower systemic exposure and greater ease of use for patients. The molecular structure of the compound ultimately dictates the ability of the drug to cross the epithelium of the tissue to which the product is applied. For cutaneous application, selection of the components of the formulation dictates the maximum skin permeation that the formulator can achieve. Creams, lotions, gels, ointments, foams and solutions are just a few of the more familiar forms of topical roflumilast formulations that often contain completely dissolved active pharmaceutical ingredients (API) for application to the skin as disclosed in the '298 patent (col 12, lines 37-64). For treatment of such dermatoses, roflumilast emulsions, suspensions, gels or solutions for topical application have been described, although the low solubility of the compound has limited those applications.

Several approaches have been proposed for enhancing the solubility of active ingredients with low aqueous solubility. These approaches include particle size reduction, hydrotrophy, precipitation inhibitors (e.g. HPMC, PVP, PVA, PEG) complexation, solvent deposition, alteration of pH, lyophilization, surfactants, co-solvency, micro emulsions, solid dispersion and solvate formation. WO 2013/030789 discloses PDE-IV inhibitor with poor water solubility in combination with a binder selected from a saccharide (e.g. sucrose, lactose, starches, microcrystalline cellulose, low-viscosity hydroxypropyl cellulose and/or a hydroxypropylmethyl cellulose), protein (e.g. gelatin) or synthetic polymer (e.g. polyethylene glycol, polyvinyl acetate, polyvinyl alcohol and propylene glycol). In U.S. Pat. No. 9,205,044 (incorporated herein by reference), the poor water solubility of roflumilast was overcome by using alkoxylated fat, specifically polyoxyethylated 12-hydroxystearic acid, as a co-solvent. In EP 1511516B1 (corresponding to published U.S. application Ser. No. 14/075,035 incorporated herein by reference), the low water solubility of roflumilast was overcome in topical emulsion formulations (creams) by formulating with polyethylene glycol 400 (PEG 400) in concentrations over 62% (w/w) while keeping water weight percentages under 10%. U.S. Pat. No. 7,951,398 (incorporated herein by reference) discloses a solid dispersion of roflumilast, which is indicated as a poorly soluble drug, wherein roflumilast is dispersed in a matrix comprising fatty alcohol, triglyceride and fatty acid ester at high temperature, and then cooled and granulated with a hydrophilic polymer. U.S. Pat. No. 6,074,670 discloses a composition of fenofibrate, which is a poorly soluble drug, which has improved dissolution. The composition includes a hydrophilic polymer and a surfactant, wherein the fenobibrate was granulated with solution of a hydrophilic polymer such as polyvinylpyrrolidone which results in an improved dissolution profile. U.S. Pat. No. 8,431,154 (incorporated herein by reference) discloses a composition of Roflumilast with improved release and improved pharmacokinetic profile by using an aqueous solution of polyvinylpyrrolidone (PVP) for granulation of roflumilast by preparing a solid solution or solid dispersion. Published U.S. application Ser. No. 14/114,541 (incorporated herein by reference) discloses that novel PI3K inhibitors can be combined with soluble macromolecular entities, such as cyclodextrin and suitable derivatives thereof or polyethylene glycol-containing polymers in order to improve their solubility, dissolution rate, taste-masking, bioavailability and/or stability.

WO 2015/132708 discloses the use of a multiparticulate composition containing roflumilast and an inert component. The inert component is prepared by granulation and then combined with the roflumilast resulting in a composition with improved dissolution. The composition preferably includes a polyvinyl alcohol as part of the inert component, One technique for increasing solubility of an active ingredient has been to blend an alcohol or a glycol with water to create a solvent blend that is less polar than water. Because pharmaceutically acceptable alcohols, such as ethanol or isopropyl alcohol, are not desirable excipients for topical application to inflammatory dermatoses due to the tendency to further irritate inflamed skin, propylene glycol is a co-solvent frequently used in topical creams and gels for the treatment of psoriasis or atopic dermatitis. Propylene glycol (abbreviated PG) has been used to increase the solubility of corticosteroids in topical gels, lotions and creams that tend to contain greater than 20% water and volatiles and/or less than 50% hydrocarbons, waxes, or polyols (USP <1151> Definition of Topical Emulsion). Another solvent chemically very similar to PG that was first used in an FDA-approved topical product in 2005, is diethylene glycol monoethyl ether (Tradename TRANSCUTOL®) and abbreviated DEGEE. Diethylene glycol monoethyl ether is used as a vehicle and as a solubilizer for preparing pharmaceutical compositions (for example, see U.S. applications Ser. Nos. 14/242,973; 12/846079 and 15/376,345, incorporated herein by reference). Diethylene glycol monoethyl ether is also used as a skin permeability enhancer (U.S. application Ser. Nos. 15/260,554 and 15/297,998, incorporated herein by reference) and as a surfactant (U.S. Pat. No. 9,649,302, incorporated herein by reference). Although PG has been used in many more FDA approved topical products for decades longer than DEGEE, the two solvents are remarkably similar as shown in Table 1. However, these solvents have different effects on the solubility and skin permeability of different active ingredients.

TABLE 1

Comparison of two pharmaceutically acceptable glycols for use in topical products.

| Property | DEGEE | PG |
| --- | --- | --- |
| Molecular Formula | $C_6H_{14}O_3$ | $C_3H_8O_2$ |
| Molar Mass g/mole | 134.18 | 76.1 |
| Density g/ml at 20° C. | 0.989 | 1.036 |
| Melting Point | −76° C. | −59° C. |
| Boiling Point | 198-210° C. | 187-188° C. |
| Octanol-Water Partition Coefficient (log P) | −0.43 | −0.92 |

Minghetti et. al. (J. Pharm. Sci. 96(4)814-823, 2007) determined the solubility of four salts of diclofenac in neat PG and neat DEGEE and this solubility data is summarized in Table 2.

TABLE 2

Solubility data for four salts of diclofenac taken from P. Minghetti et. al, J. Pharm. Sci 96, 814-823)

| Pharmaceutical Active | Solubility in DEGEE (µg/mL) | Solubility in PG (µg/mL) |
| --- | --- | --- |
| Sodium Diclofenac | 660 + 70 | 567 + 31 |
| Potassium Diclofenac | 709 + 52 | 898 + 79 |
| Diethylamine Diclofenac | 279 + 10 | 384 + 14 |
| Epolamine Diclofenac | 430 + 0 | 637 + 60 |

Although both solvents are considered safe for topical application up to and beyond about 50 weight percent, pharmaceutical formulations usually limit the amount of DEGEE or PG to about 30% due to irritation seen in a subset of patients. Thus, these glycols are almost always blended with water when formulating topical gels or emulsions (creams or lotions). When blending two solvents the ideal solubility of any blend can be calculated based on the solubility of the active ingredient in each of the separate solvents. The calculated "ideal" solubility will best agree with the observed solubility when the physical properties of the two solvents are closely aligned. The J. W. Lorimer publication on the thermodynamics of solubility in mixed solvent systems (Pure & Appl. Chem. 65(2)183-191, 1993) showed exact correlation between ideal and measured solubility of NaCl when dissolved in blends of water ($H_2O$) and deuterium oxide ($D_2O$) and reasonable correlations for NaCl data in blends of water and ethylene glycol. For the blend of water and ethylene glycol, the poorest correlation between calculated "ideal" solubility and observed solubility occurred at equimolar blends of the two solvents with the observed saturation solubility being 18-fold lower than the calculated ideal solubility (J. Solution Chem., 14, 635 (1985)). Lorimer uses classical thermodynamics to derive the ideal solubility (shown as $\ln(m_s^{(12)}/m°)$ in the paper) based on the chemical potential of the solute (API) in solvent which has a linear correlation to mole fraction of the solvent blend.

The ability to calculate the expected solubility at any ratio of the solvent blend after experimentally determining drug solubility in each of the two neat solvents facilitates formulation of a topical product. Usually a target concentration has been determined based on the potency of the API. Highly potent drug active ingredients, such as some of the corticosteroids or calcipotriene, will have target concentrations in a topical product of 0.05% to 0.5%. Most topical products will be around 2%. Since maximum thermodynamic driving force across the skin occurs at saturation, the skilled formulator will want to know saturation drug concentrations in solvent blends over a range of solvent blend ratios. By calculating ideal solubility values before setting up a full matrix of experimental solubility determinations, the number of experiments can be reduced from a few hundred to less than 100 observed saturated drug solubility determinations.

SUMMARY OF THE INVENTION

In accordance with the present invention, it has been discovered that surprisingly high concentrations of roflumilast can be dissolved in solvent blends of diethylene glycol monoethyl ether (DEGEE) and water. This dramatically increased solubility of roflumilast was maintained when the solvent blend was formulated with up to 0.5% roflumilast in an emollient cream.

BRIEF DESCRIPTION OF THE DRAWINGS

The patent or application file contains at least one figure executed in color. Copies of this patent or patent application publication with color figures will be provided by the Office upon request and payment of the necessary fee.

DESCRIPTION OF THE INVENTION

Figure 1:
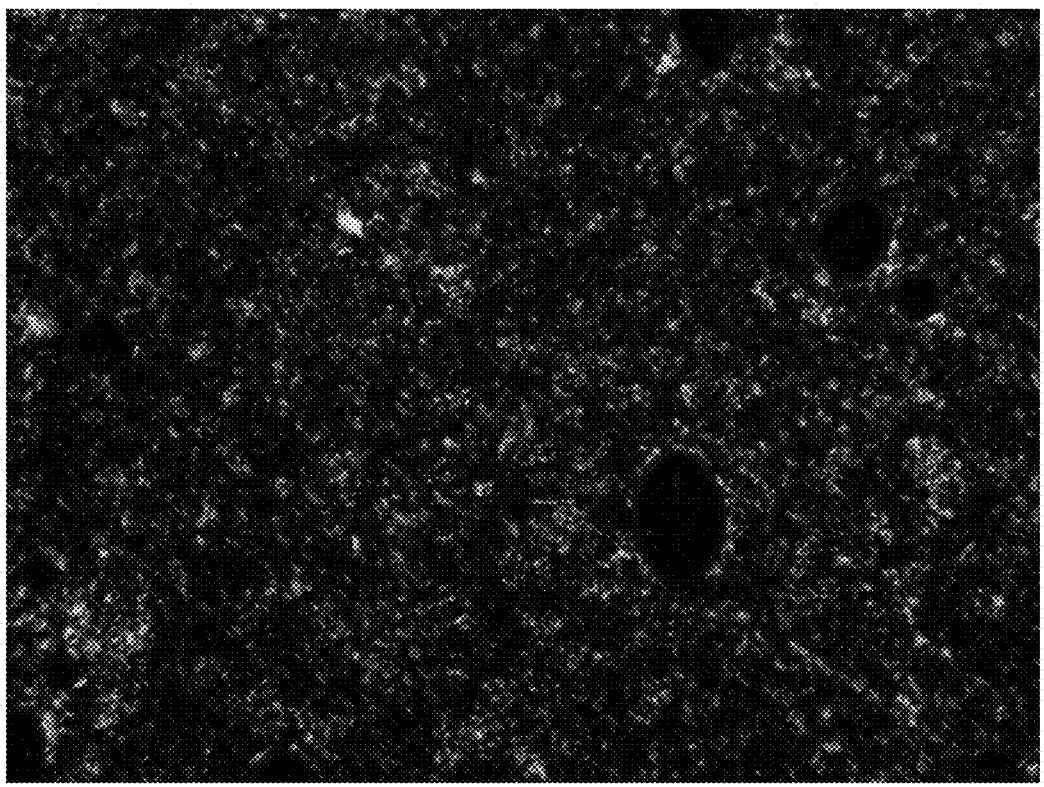
FIG. 1 shows a Microscopic View of a sample of formulation 1 using a polarized light microscope equipped with a 10× objective.

Roflumilast is a compound of the formula (I)

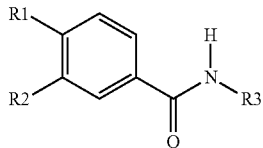

(I)

wherein R1 is difluoromethoxy, R2 is cyclopropylmethoxy and R3 is 3,5-dichloropyrid-4-yl.

This compound has the chemical name N-(3,5-dichloro-pyrid-4-yl)-3-cyclopropylmethoxy-4-difluoromethoxybenz-amid-e (INN: roflumilast). Roflumilast can be prepared by methods known in the art (e.g. see the '298 patent and U.S. application Ser. No. 14/075,035).

Diethylene glycol monoethyl ether is a compound of the formula (II)

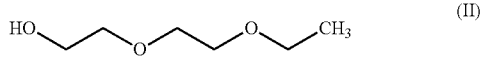

(II)

The present invention is directed to pharmaceutical compositions of roflumilast dissolved in blends of diethylene glycol monoethyl ether (DEGEE, Gattefosse Tradename TRANSCUTOL®) and water, optionally including one or more pharmaceutically acceptable carriers. Any suitable grade of TRANSCUTOL® can be used including TRANSCUTOL®P, TRANSCUTOL®HP, TRANSCUTOL®V and TRANSCUTOL®CG. This blend of DEGEE and water can undergo the addition of excipients and further processing to form a range of pharmaceutical dosage forms and maintain dissolved or molecularly dispersed roflumilast over the shelf life of the drug product.

The present invention is particularly useful for topical formulations. The topical roflumilast pharmaceutical product formulations that could be based on DEGEE-water blends are defined in U.S. Pharmacopeia USP <1151> and include aerosols, foams, sprays, emulsions (which can also be called creams, lotions, or ointments), gels (two phase or single phase), liquids, ointments, pastes, shampoos, suspensions, and systems. These are typical dosage forms containing pharmaceutically active ingredients for topical application to mammals, including humans.

Topical application refers to dosing the skin, hair or nails of a patient that will benefit from treatment with a pharmaceutical product. Topical can also mean application to the epithelium of the patient for localized delivery. This would include ophthalmic, otic, oral mucosa, vaginal mucosa, rectal mucosa or urethral application of roflumlast. The broadest definition of topical would include using the epithelium of a patient as a route of administration to obtain therapeutic systemic levels of the active ingredient. This definition of topical is often referred to as transdermal delivery of therapeutic active ingredients.

DEGEE is often formulated as 10-30% (w/w), preferably 15-20% (w/w), in topical formulations. Likewise, water is formulated as about 20-90% (w/w) in topical products. For blends of DEGEE and water the ratio can range from 1:10 to 20:1. Preferably the DEGEE:water ratio is 1:4 to 9:1 in a formulation containing roflumilast.

Generally, DEGEE-water blends can be used to dissolve up to 2.0% roflumilast (in the finished product) or preferably up to 0.5% roflumilast (in the finished product). The finished product is preferably in one of the following forms:

An oil-in-water emulsion: The topical product may be an emulsion comprising a discrete hydrophobic phase and a continuous aqueous phase that includes the DEGEE-water blend and optionally one or more polar hydrophilic excipients as well as solvents, co-solvents, salts, surfactants, emulsifiers, and other components. These emulsions may include water-soluble or water-swellable polymers that help to stabilize the emulsion.

A water-in-oil emulsion: The compositions may be formulations in which roflumilast is incorporated into an emulsion that includes a continuous hydrophobic phase and an aqueous phase that includes the DEGEE-water blend and optionally one or more polar hydrophilic carrier(s) as well as salts or other components. These emulsions may include oil-soluble or oil-swellable polymers as well as one or more emulsifier(s) that help to stabilize the emulsion.

For both oil-in-water and water-in-oil emulsions, order of addition may be important. Roflumilast can be added pre-dissolved in the continuous aqueous phase containing the DEGEE-water blend. Likewise, roflumilast can be pre-dissolved in the hydrophobic discrete phase of the emulsion that is then mixed with the DEGEE-water blend and optional hydrophilic excipients that do not contain the active ingredient. Roflumilast can be pre-dissolved in both the oil phase and water phase of the emulsion or added pre-dissolved in DEGEE or a DEGEE-water blend after the emulsion has been formed. Some emulsions undergo phase inversion over a specific temperature range during cooling of the emulsion. Thus, roflumilast may be added to a water-in-oil emulsion above the phase inversion temperature, with the final drug product being an oil-in-water emulsion at controlled room temperature, or vice versa.

Thickened aqueous gels: These systems include the DEGEE-water blend with dissolved roflumilast and optionally one or more polar hydrophilic carrier(s) such as hexylene glycol which has been thickened by suitable natural, modified natural, or synthetic thickeners as described below. Alternatively, the thickened aqueous gels can be thickened using suitable polyethoxylate alky chain surfactants or other nonionic, cationic, or anionic systems.

Thickened hydroalcoholic gels: These systems include the DEGEE-water-alcohol blend with dissolved roflumilast and optionally one or more polar hydrophilic carrier(s) such as hexylene glycol as the polar phase which has been thickened by suitable natural, modified natural, or synthetic polymers such as described below. Alternatively, the thickened hydroalcoholic gels can be thickened using suitable polyethoxylate alky chain surfactants or other nonionic, cationic, or anionic systems. The alcohol can be ethanol, isopropyl alcohol or other pharmaceutically acceptable alcohol.

A hydrophilic or hydrophobic ointment: The compositions are formulated with a hydrophobic base (e.g. petrolatum, thickened or gelled water insoluble oils, and the like) and optionally have a minor amount of the DEGEE-water blend with dissolved roflumilast. Hydrophilic ointments generally contain one or more surfactants or wetting agents.

Solvents

Compositions of the present invention may include one or more solvents or co-solvents to obtain the desired level of active ingredient solubility in the product. The solvent may also modify skin permeation or activity of other excipients contained in a topical product. Solvents include but are not limited to acetone, ethanol, benzyl alcohol, butyl alcohol, diethyl sebacate, diethylene glycol monoethyl ether, diisopropyl adipate, dimethyl sulfoxide, ethyl acetate, isopropyl alcohol, isopropyl isostearate, isopropyl myristate, N-methyl pyrrolidinone, propylene glycol and SD alcohol.

Moisturizers

Compositions of the present invention may include a moisturizer to increase the level of hydration. For emulsions, the moisturizer is often a component of the discrete or continuous hydrophobic phase. The moisturizer can be a hydrophilic material including humectants or it can be a hydrophobic material including emollients. Suitable moisturizers include but are not limited to: 1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, ethylhexyl hydroxystearate, fatty acids, glyceryl isostearate, glyceryl laurate, glyceryl monostearate, glyceryl oleate, glyceryl palmitate, glycol distearate, glycol stearate, isostearic acid, isostearyl alcohol, lanolin, mineral oil, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, and stearyl alcohol.

Surfactants and Emulsifiers

Compositions according to the present invention can optionally include one or more surfactants to emulsify the composition and to help wet the surface of the active ingredients or excipients. As used herein the term "surfactant" means an amphiphile (a molecule possessing both polar and nonpolar regions which are covalently bound) capable of reducing the surface tension of water and/or the interfacial tension between water and an immiscible liquid. Surfactants include but are not limited to alkyl aryl sodium sulfonate, Amerchol-CAB, ammonium lauryl sulfate, apricot kernel oil PEG-6 esters, Arlacel, benzalkonium chloride, Ceteareth-6, Ceteareth-12, Ceteareth-15, Ceteareth-30, cetearyl alcohol/ceteareth-20, cetearyl ethylhexanoate, ceteth-10, ceteth-10 phosphate, ceteth-2, ceteth-20, ceteth-23, choleth-24, cocamide ether sulfate, cocamine oxide, coco betaine, coco diethanolamide, coco monoethanolamide, coco-caprylate/caprate, dicetyl phosphate, disodium cocoamphodiacetate, disodium laureth sulfosuccinate, disodium lauryl sulfoacetate, disodium lauryl sulfosuccinate, disodium oleamido monoethanolamine sulfosuccinate, docusate sodium, laureth-2, laureth-23, laureth-4, lauric diethanolamide, lecithin, mehoxy PEG-16, methyl gluceth-10, methyl gluceth-20, methyl glucose sesquistearate, oleth-2, oleth-20, PEG 6-32 stearate, PEG-100 stearate, PEG-12 glyceryl laurate, PEG-120 methyl glucose dioleate, PEG-15 cocamine, PEG-150 distearate, PEG-2 stearate, PEG-20 methyl glucose sesqustearate, PEG-22 methyl ether, PEG-25 propylene glycol stearate, PEG-4 dilaurate, PEG-4 laurate, PEG-45/dodecyl glycol copolymer, PEG-5 oleate, PEG-50 Stearate, PEG-54 hydrogenated castor oil, PEG-6 isostearate, PEG-60 hydrogenated castor oil, PEG-7 methyl ether, PEG-75 lanolin, PEG-8 laurate, PEG-8 stearate, Pegoxol 7 stearate, pentaerythritol cocoate, poloxamer 124, poloxamer 181, poloxamer 182, poloxamer 188, poloxamer 237 poloxamer 407, polyglyceryl-3 oleate, polyoxyethylene alcohols, polyoxyethylene fatty acid esters, polyoxyl 20 cetostearyl ether, polyoxyl 40 hydrogenated castor oil, polyoxyl 40 stearate, polyoxyl 6 and polyoxyl 32, polyoxyl glyceryl stearate, polyoxyl stearate, polysorbate 20, polysorbate 40, polysorbate 60, polysorbate 65, polysorbate 80, PPG-26 oleate, PROMULGEN™ 12, propylene glycol diacetate, propylene glycol dicaprylate, propylene glycol monostearate, sodium xylene sulfonate, sorbitan monooleate, sorbitan monopalmitate, sorbitan monostearate, steareth-2, steareth-20, steareth-21, steareth-40, tallow glycerides, and emulsifying wax.

Polymers and Thickeners

For certain applications, it may be desirable to formulate a topical product that is thickened with soluble, swellable, or insoluble organic polymeric thickeners such as natural and synthetic polymers or inorganic thickeners including but not limited to acrylates copolymer, carbomer 1382, carbomer copolymer type B, carbomer homopolymer type A, carbomer homopolymer type B, carbomer homopolymer type C, caroboxy vinyl copolymer, carboxymethylcellulose, carboxypolymethylene, carrageenan, guar gum, hydroxyethyl cellulose, hydroxypropyl cellulose, microcrystalline wax, and methylcellulose.

Additional Components

Compositions according to the present invention may be formulated with additional components conventionally found in cosmetic and pharmaceutical topical products. Additional components include but are not limited to antifoaming agents, preservatives, antioxidants, sequestering agents, stabilizers, buffers, pH adjusting solutions, skin penetration enhancers, film formers, dyes, pigments, fragrances and other excipients to improve the stability or aesthetics of the product. In a preferred embodiment, hexylene glycol is added to inhibit changes in particle size distribution over the shelf life of the composition. Hexylene glycol can be added between 0.1% and 20% on a weight/weight basis, preferably between 0.25% and 8% on a weight/weight basis and most preferably between 0.5% and 2% on a weight/weight basis.

Compositions according to the present invention may be formulated with additional active agents depending on the condition to be treated. The additional active agents include but are not limited to Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, Adalimumab, Ustekinumab, Infliximab, bronchodialators (e.g. beta-agonists, anticholinergics, theophylline), and antibiotics (e.g. erythromycin, ciprofloxacin, metronidazole).

Administration and Dosage

The compositions according to the present invention can be administered by any suitable administration route including but not limited to oral, rectal, parenteral (e.g. intradermal, subcutaneous, intramuscular, intravenous, intramedullary, intra arterial, intrathecal, epidural) ocular, inhalation, nebulization, cutaneously (topically), transdermally, and mucosally (e.g. sublingual, buccal, nasally). In a preferred embodiment, the composition is administered topically.

Suitable pharmaceutical dosage forms include but are not limited to emulsions, suspensions, sprays, oils, ointments, fatty ointments, creams, pastes, gels, foams transdermal patches and solutions (e.g. injectable, oral).

The composition preferably contains roflumilast, salts of roflumilast, the N-oxide of roflumilast or salts thereof in an amount of 0.005-2% w/w, more preferably 0.05-1% w/w, and most preferably 0.1-0.5% w/w per dosage unit.

The composition preferably contains diethylene glycol monoethyl ether in an amount of between 5% and 50% w/w, more preferably between 20% and 30% w/w and most preferably between 22.5% and 27.5% w/w.

The composition can be administered one or more times per day, preferably the composition is administered 1-2 times per day.

The composition can be used in veterinary and in human medicine for the treatment and prevention of all diseases regarded as treatable or preventable by using roflumilast, including but not limited to acute and chronic airway disorders; proliferative, inflammatory and allergic dermatoses; disorders which are based on an excessive release of TNF and leukotrienes; disorders of the heart which can be treated by PDE inhibitors; inflammations in the gastrointestinal system or central nervous system; disorders of the eye; arthritic disorders; and disorders which can be treated by the tissue-relaxant action of PDE inhibitors. Preferably, the composition is used to treat proliferative, inflammatory and allergic dermatoses such as psoriasis (vulgaris), eczema, acne, Lichen simplex, sunburn, pruritus, alopecia areata, hypertrophic scars, discoid lupus erythematosus, and pyodermias.

The following examples are provided to enable those of ordinary skill in the art to make and use the methods and compositions of the invention. These examples are not intended to limit the scope of what the inventors regard as their invention. Additional advantages and modifications will be readily apparent to those skilled in the art.

EXAMPLE 1

Roflumilast (Batch A14367P from Interquim S.A.), 0.0061 grams, was weighed into a liquid scintillation vial. PG (propylene glycol, Spectrum Chemical lot IEC0004) was added dropwise with mixing to the vial containing roflumilast. After mixing each addition of PG, the tightly capped vial was returned to a water bath set at 25° C. It required 1.9332 grams of PG to completely dissolve the 0.0061 grams of roflumilast which equals the observed saturation solubility of 0.3 w/w % roflumilast in PG at 25° C. The cited value of 0.53 mg/l (at 21° C.) in WO95/01338 was used as the observed value for saturation solubility of roflumilast in water which equals 0.000053 w/w %. Using the equations of Lorimer, the observed saturation solubility in PG of 0.3% roflumilast and the observed saturation solubility in water of 0.000053%, the calculated ideal solubility of roflumilast in equimolar PG:Water is 0.0040 w/w %.

2.3200 grams of an equimolar blend of PG (Spectrum Chemical lot IEC0004) and distilled water was prepared and added to a scintillation vial containing 0.0012 grams of roflumilast (Batch A14367P from Interquim S.A.). After equilibrating to 25° C. the roflumilast completely dissolved to form a 0.052% solution. An equimolar blend is 80.7% PG and 19.3% water on a weight/weight percent basis. The addition of 2.2696 grams of equimolar PG:Water did not completely dissolve 0.0017 grams of roflumilast at 25° C. (0.075% roflumilast). The experimentally determined, observed saturation solubility of roflumilast equimolar PG:Water at 25° C. was 0.06 w/w %.

At 25° C. the observed saturation solubility of roflumilast in equimolar PG:Water was 15-fold greater than the calculated ideal solubility of roflumilast in equimolar PG:Water blends (80.7:19.3 PG:Water w/w).

EXAMPLE 2

Roflumilast (Batch A14367P from Interquim S.A.), 0.0205 grams, was weighed into a liquid scintillation vial. DEGEE (Transcutol P, lot 146063, Gattefosse) was added dropwise with mixing to the vial containing roflumilast. After mixing each addition of DEGEE, the tightly capped vial was returned to a water bath set at 25° C. It required 0.2699 grams of DEGEE to completely dissolve the 0.0205 grams of roflumilast which equals an observed saturation solubility of 7.1 w/w % roflumilast in DEGEE at 25° C. The cited value of 0.53 mg/l (at 21° C.) in WO95/01338 was used as the observed value for saturation solubility of roflumilast in water which equals 0.000053 w/w %. Using the equations of Lorimer, the observed saturation solubility in DEGEE of 7.1% roflumilast and the observed saturation solubility in water of 0.000053%, the calculated ideal solubility of roflumilast in equimolar DEGEE:Water is 0.019 w/w %.

0.0111 grams of roflumilast (Batch A14367P from Interquim S.A.) was weighed into a liquid scintillation vial. An equimolar blend of DEGEE (Transcutol P, lot 146063, Gattefosse) and distilled water was prepared and added dropwise with mixing to the vial containing roflumilast. An equimolar blend is 88.3% DEGEE and 11.7% water on a weight/weight percent basis. After mixing each addition of equimolar DEGEE:Water, the tightly capped vial was returned to a water bath set at 25° C. 0.0111 grams of roflumilast did not dissolve after addition of 0.2337 grams of equimolar DEGEE:Water (4.53% roflumilast) but did dissolve after the addition of 0.2477 grams of equimolar DEGEE:Water (4.29% roflumilast). The experimentally determined saturation solubility of roflumilast equimolar DEGEE:Water at 25° C. was observed to be 4.4 w/w %.

At 25° C. the observed saturation solubility of roflumilast in equimolar DEGEE:Water was 232-fold greater than the calculated ideal solubility of roflumilast in equimolar DEGEE:Water blends (88.3:11.7 DEGEE:Water w/w).

EXAMPLE 3

Figure 2:
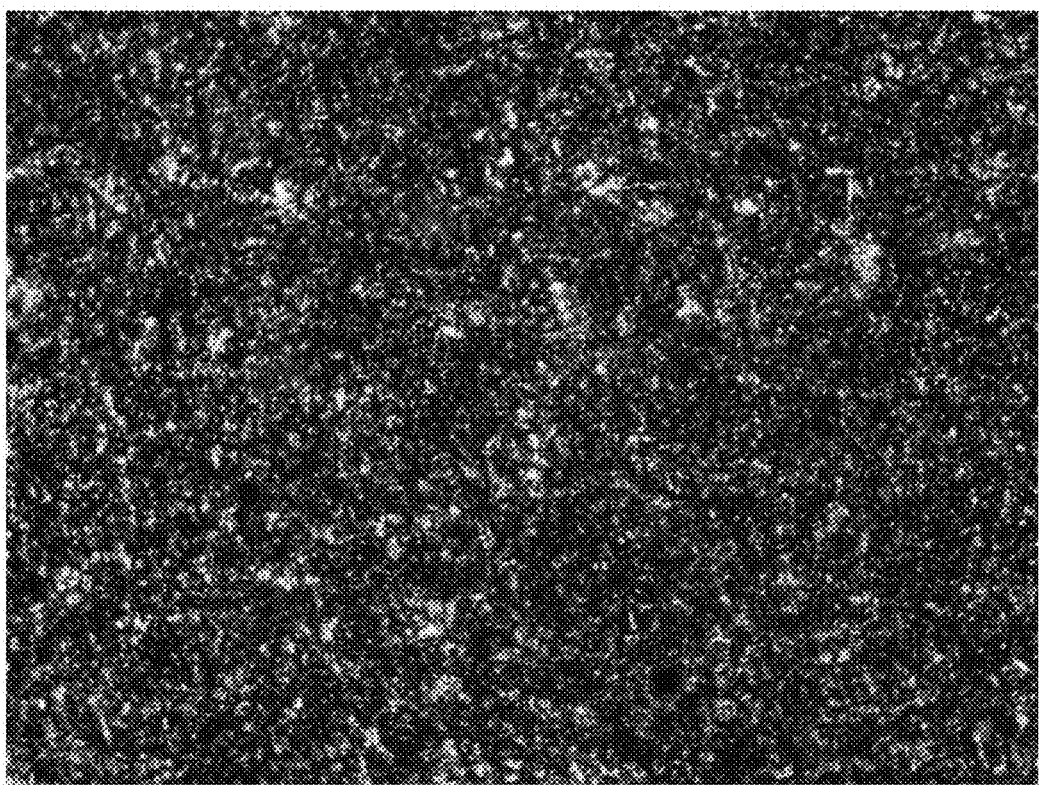
FIG. 2 shows a Microscopic View of a sample of formulation 2 using a polarized light microscope equipped with a 10× objective.
Figure 3:
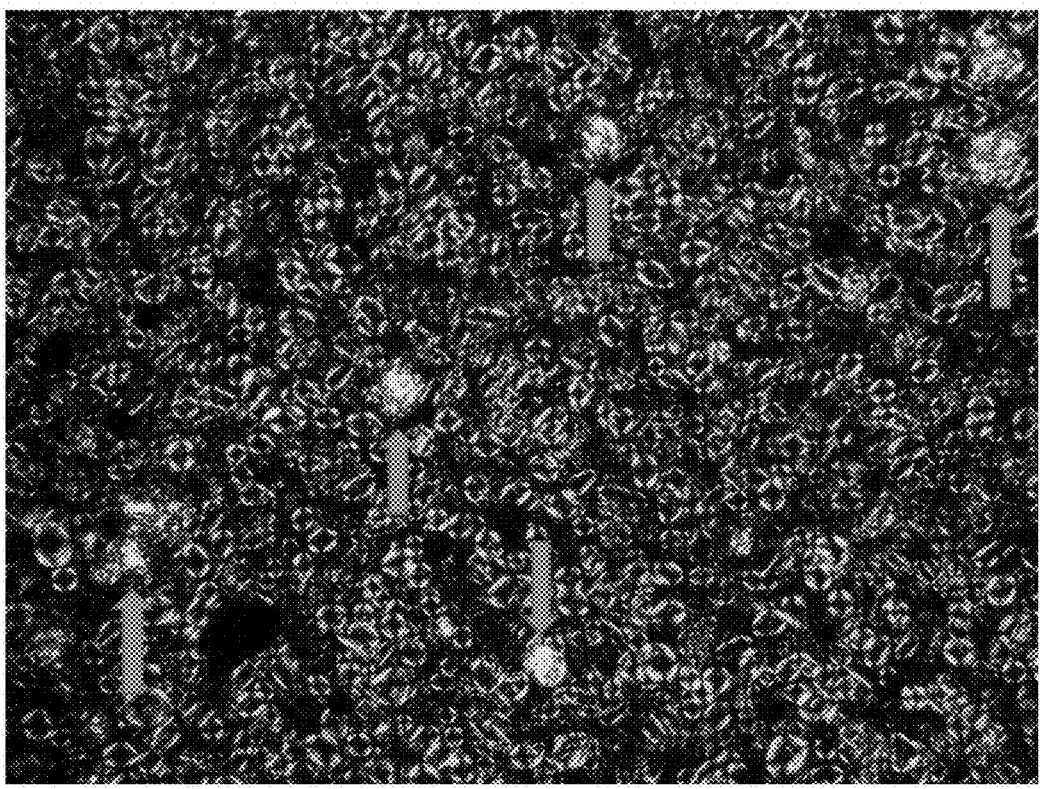
FIG. 3 shows a Microscopic View of a sample of formulation 3 using a polarized light microscope equipped with a 10× objective. The blue arrows indicate five of the largest undissolved roflumilast particles in the photomicrographs of these five creams
Figure 4:
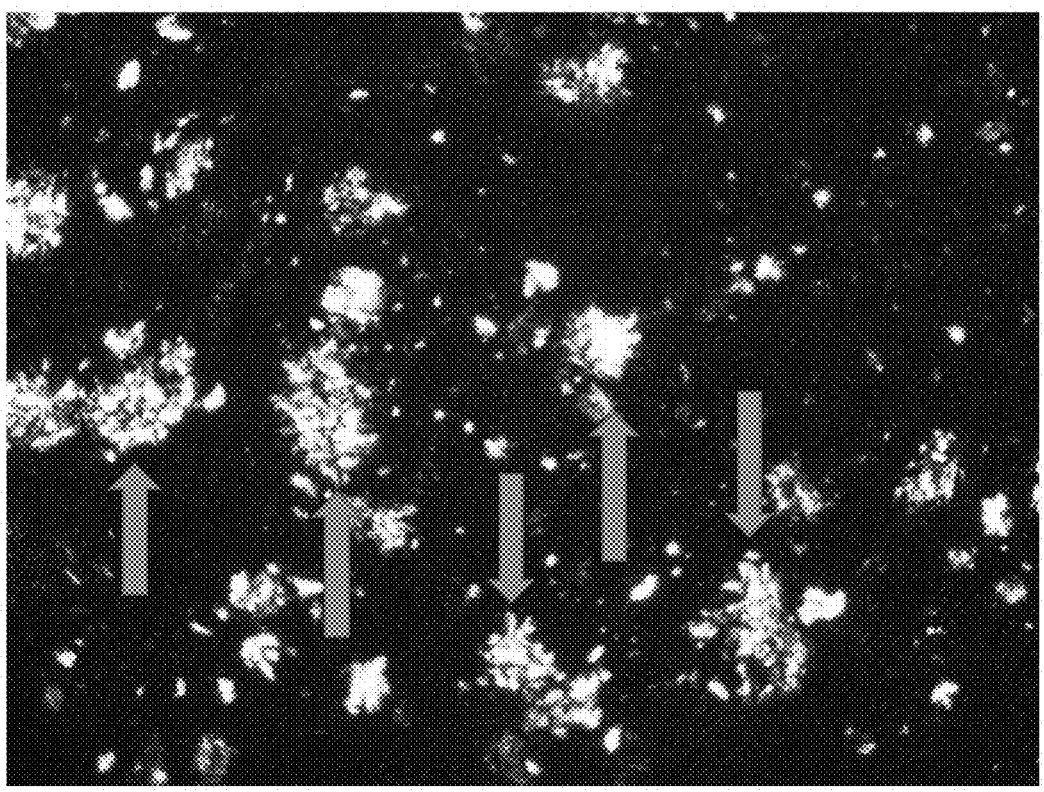
FIG. 4 shows a Microscopic View of a sample of formulation 4 using a polarized light microscope equipped with a 10× objective. The blue arrows indicate five of the largest undissolved roflumilast particles in the photomicrographs of these five creams
Figure 5:
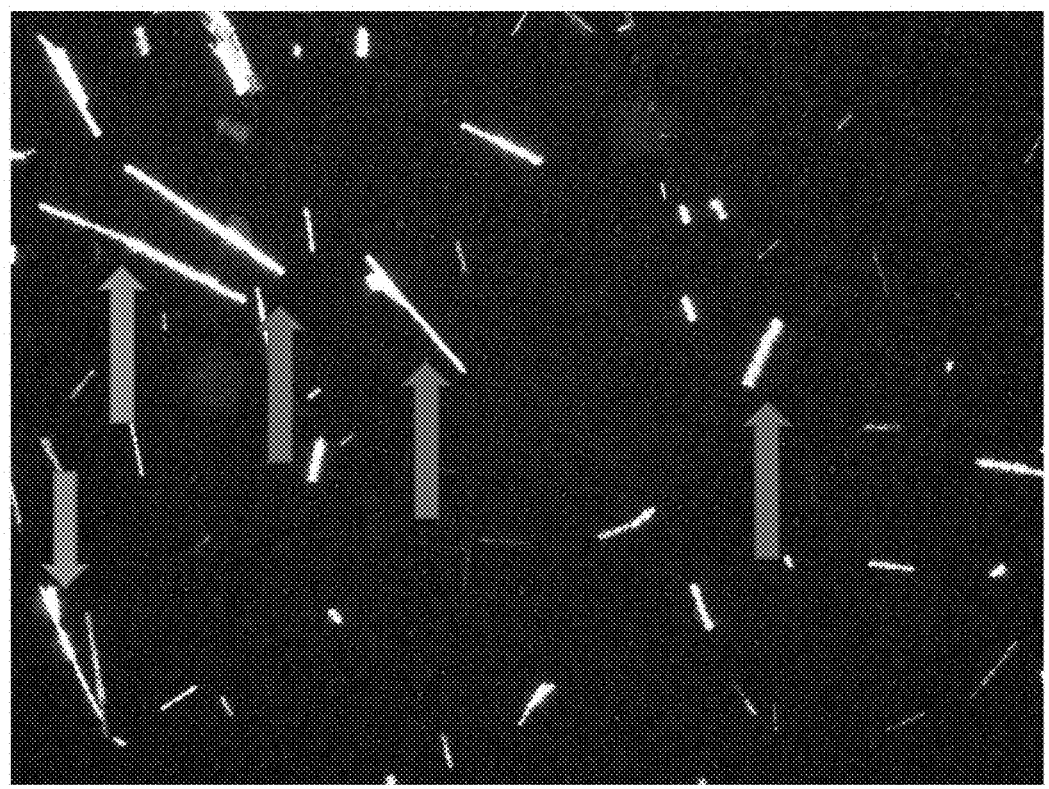
FIG. 5 shows a Microscopic View of a sample of formulation 5 using a polarized light microscope equipped with a 10× objective. The blue arrows indicate five of the largest undissolved roflumilast particles in the photomicrographs of these five creams.

0.5% roflumilast creams were prepared according to the following formulations. After at least one month of storage in a tightly closed glass container, a thin smear of cream was loaded onto a glass microscope slide and a coverslip was placed on the sample. The Microscopic View of the sample using a polarized light microscope equipped with a 10× objective was obtained (FIGS. 1-5). The Microscopic View photomicrographs were examined to determine if undissolved roflumilast was present in the cream. The blue arrows indicate five of the largest undissolved roflumilast particles in the photomicrographs of these five creams. Only the two creams containing Transcutol (25%) did not contain undissolved active.

| Formulation 1 | |
| --- | --- |
| Roflumilast | 0.5% w/w |
| White Petrolatum | 10.0% w/w |

Formulation 1

| | |
|---|---|
| Isopropyl Palmitate | 5.0% w/w |
| Crodafos ™ CES* | 10.0% w/w |
| Hexylene glycol | 8.0% w/w |
| N-methyl pyrrolidone | 12.0% w/w |
| Diethylene glycol monoethyl ether (Transcutol P) | 25.0% w/w |
| Methylparaben | 0.2% w/w |
| Propylparaben | 0.05% w/w |
| Purified Water | q.s. ad 100 (29.25%) |

*(Tradename for the Croda emulsifier blend of cetearyl alcohol, dicetyl phosphate and ceteth-10 phosphate)

Formulation 2

| | |
|---|---|
| Roflumilast | 0.5% w/w |
| White Petrolatum | 10.0% w/w |
| Isopropyl Palmitate | 5.0% w/w |
| Crodafos ™ CES | 10.0% w/w |
| Hexylene glycol | 2.0% w/w |
| Diethylene glycol monoethyl ether (Transcutol P) | 25.0% w/w |
| Methylparaben | 0.2% w/w |
| Propylparaben | 0.05% w/w |
| Purified Water | q.s. ad 100 (47.25%) |

Formulation 3

| | |
|---|---|
| Roflumilast | 0.5% w/w |
| Glycerol Monostearate | 8.0% w/w |
| Emulgade ® A6** | 4.0% w/w |
| PEG 400 | 62.5% w/w |
| Purified Water | q.s. ad 100 (25.0%) |

**(Tradename for the BASF emulsifier blend of Ceteareth-6 and Stearyl Alcohol)

Formulation 4

| | |
|---|---|
| Roflumilast | 0.5% w/w |
| Diisopropyl Adipate | 15.0% w/w |
| POE-7 Cocoyl Glycerides | 13.5% w/w |
| Cetyl Alcohol | 5.0% w/w |
| Parafin | 1.0% w/w |
| Lanolin | 2.0% w/w |
| Methyl Paraben | 0.2% w/w |
| PEG 400 | 3.0% w/w |
| Xanthan Gum | 0.3% w/w |
| Disodium EDTA | 0.1% w/w |
| Solan ™-75 PA*** | 3.0% w/w |
| Purified Water | q.s. ad 100 (56.4%) |

***(Tradename for the Croda emulsifier PEG-75 Lanolin)

Formulation 5

| | |
|---|---|
| Roflumilast | 0.5% w/w |
| Diethyl Sebacate | 10.0% w/w |
| Light Mineral Oil | 0.7% w/w |
| Sorbitan Monooleate | 0.1% w/w |
| Propylene glycol | 7.5% w/w |
| Methylparaben | 0.17% w/w |
| Propylparaben | 0.03% w/w |
| Edetate Disodium | 0.05% w/w |
| Pemulen TR-1 | 0.4% w/w |
| Carbopol 981 | 0.6% w/w |
| 1N sodium hydroxide | 3.0% w/w |
| Purified Water | q.s. ad 100 (76.95%) |

The invention claimed is:

1. A pharmaceutical composition consisting of roflumilast, white petrolatum, isopropyl palmitate, an emulsifier blend of cetearyl alcohol, dicetyl phosphate and ceteth-10 phosphate, hexylene glycol, N-methyl pyrrolidone, diethyl glycol monoethyl ether, methylparaben, propylparaben and water in the following proportions:
   Roflumilast 0.5% w/w
   White Petrolatum 10.0% w/w
   Isopropyl Palmitate 5.0% w/w
   Emulsifier blend 10.0% w/w
   Hexylene glycol 8.0% w/w
   N-methyl pyrrolidone 12.0% w/w
   Diethylene glycol monoethyl ether 25.0% w/w
   Methylparaben 0.2% w/w
   Propylparaben 0.05% w/w
   Purified Water q.s. ad 100.

2. A pharmaceutical composition consisting of roflumilast, white petrolatum, isopropyl palmitate, an emulsifier blend of cetearyl alcohol, dicetyl phosphate and ceteth-10 phosphate, hexylene glycol, diethyl glycol monoethyl ether, methylparaben, propylparaben, and water, in the following proportions:
   Roflumilast 0.5% w/w
   White Petrolatum 10.0% w/w
   Isopropyl Palmitate 5.0% w/w
   Emulsifier blend 10.0% w/w
   Hexylene glycol 2.0% w/w
   Diethylene glycol monoethyl ether 25.0% w/w
   Methylparaben 0.2% w/w
   Propylparaben 0.05% w/w
   Purified Water q.s. ad 100
   wherein said composition does not contain undissolved roflumilast.

* * * * *